United States Patent [19]

Porter et al.

[11] 4,087,460
[45] May 2, 1978

[54] SUBSTITUTED N-ALKOXY-N-SUBSTITUTED-2,6-DINITROANILINES AND INTERMEDIATES FOR THE PREPARATION THEREOF

[75] Inventors: Herschel D. Porter; James C. Williams, both of Indianapolis, Ind.

[73] Assignee: Eli Lilly and Company, Indianapolis, Ind.

[21] Appl. No.: 810,229

[22] Filed: Jun. 27, 1977

[51] Int. Cl.$^2$ .................... C07C 93/00; A01N 9/20
[52] U.S. Cl. ........................ 260/574; 71/121
[58] Field of Search ............. 260/574, 577; 71/121

[56] References Cited

U.S. PATENT DOCUMENTS

| 3,067,254 | 12/1962 | Wilder | 260/576 |
|---|---|---|---|
| 3,102,803 | 9/1963 | Wilder | 71/2.3 |
| 3,403,180 | 9/1968 | Soper | 260/577 |
| 3,716,585 | 2/1973 | Strong et al. | 260/574 |
| 3,726,923 | 4/1973 | Foster et al. | 260/577 |
| 3,849,107 | 11/1974 | Fischer | 71/92 |
| 3,920,742 | 11/1975 | Lutz et al. | 260/577 |
| 3,989,508 | 11/1976 | Fischer | 71/120 |
| 3,991,116 | 11/1976 | Damiano | 260/577 |
| 4,042,628 | 8/1977 | Kiehs et al. | 260/577 |

FOREIGN PATENT DOCUMENTS

| 2,007,051 | 8/1971 | Germany | 71/121 |
|---|---|---|---|
| 2,361,463 | 6/1974 | Germany | 71/121 |
| 41-14998 | 8/1966 | Japan | 71/121 |

*Primary Examiner*—Daniel E. Wyman
*Assistant Examiner*—John J. Doll
*Attorney, Agent, or Firm*—Dwight E. Morrison; Arthur R. Whale

[57] ABSTRACT

A new class of 2,6-dinitroanilines substituted on the anilino nitrogen with alkoxy and alkyl groups, which compounds are active as herbicides and plant growth regulators, and intermediates useful for the preparation thereof.

12 Claims, No Drawings

SUBSTITUTED N-ALKOXY-N-SUBSTITUTED-2,6-DINITROANILINES AND INTERMEDIATES FOR THE PREPARATION THEREOF

BACKGROUND OF THE INVENTION

1. Field of the Invention

This invention relates to new chemical compounds. More particularly, this invention relates to substituted N-alkoxy-N-substituted-2,6-dinitroanilines and to intermediates useful for the preparation thereof.

2. Description of the Prior Art

Various 2,6-dinitroanilines have been described in the chemical literature. Hantzsch, *Deutsche Chemische Gesellschaft Berichte*, 43, 1662–1685 (1910) discloses N,N-dipropyl-4-methyl-2,6-dinitroaniline and N,N-dimethyl-4-methyl-2,6-dinitroaniline. Joshi et al., C.A. 28, 469 (1934) discloses N,N-dimethyl-4-iodo-2,6-dinitroaniline, N,N-dimethyl-4-bromo-2,6-dinitroaniline, 4-iodo-2,6-dinitrophenylpiperidine, and 4-bromo-2,6-dinitrophenylpiperidine. Borsche et al., C.A. 5, 2079 (1911) discloses 2,6-dinitrophenylpiperidine. Daudt et al. U.S. Pat. No. 2,212,825, disclose a number of 2,6-dinitroanilines bearing a trifluoromethyl group in the 4-position.

The utility of 2,6-dinitroanilines in agriculture was first disclosed in Soper, U.S. Pat. Nos. 3,111,403; 3,257,190; 3,332,769; and 3,367,949. Soper disclosed such compounds to possess herbicidal activity, notably preemergent herbicidal activity. Following Soper, a large number of related dinitroanilines have also been shown to possess similar herbicidal activity. See, for example, U.S. Pat. Nos. 3,321,292; 3,617,251; 3,617,252; 3,672,864; 3,672,866; 3,764,624; and 3,877,924 and Belgian Pat. No. 787,939. None of the 2,6-dinitroanilines disclosed by the above-listed references possess N-alkoxy substituents.

SUMMARY OF THE INVENTION

This invention relates to novel substituted N-alkoxy-N-substituted-2,6-dinitroanilines and to intermediate compounds for the preparation thereof. The novel final products are active as herbicides and plant growth regulators. Some of the intermediate compounds also are active as herbicides.

DESCRIPTION OF THE PREFERRED EMBODIMENT

The novel compounds of this invention are of a class having the formula:

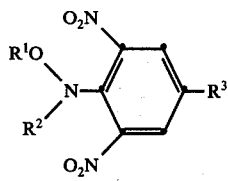

wherein
$R^1$ is methyl or ethyl;
$R^2$ is hydrogen, $C_1$–$C_3$ alkyl, or $C_3$–$C_4$ alkenyl; and
$R^3$ is methyl, ethyl, or trifluoromethyl.

In the above generic formula $C_1$–$C_3$ alkyl is represented by methyl, ethyl, n-propyl, and isopropyl; while $C_3$–$C_4$ alkenyl is represented by allyl, crotyl, and methallyl.

These novel compounds possess activity as herbicides, showing herbicidal activity in the greenhouse when applied at rates of from about 1.12 to about 8.96 kg./ha, and certain of the novel compounds are also useful as intermediates in preparation of other of the novel class of compounds of this invention.

The novel compounds of this invention are prepared by a stepwise process. This stepwise process involves first the reaction of a suitable 2,6-dinitro-4-substituted-halobenzene with an alkoxyamine hydrohalide, such as an alkoxyamine hydrochloride, in the presence of a base in a suitable solvent, to yield an N-alkoxy-2,6-dinitro-4-substituted benzene. The reaction can be carried out in a hydroxylated solvent such as methanol or ethanol, and the requisite base is a tertiary amine, such as triethylamine, or the like. The halo substituent on the 2,6-dinitro-4-substituted benzene may be bromo, chloro, fluoro, or iodo.

The preparation of an N-alkoxy-2,6-dinitro-4-substituted benzene may be illustrated as follows. 2,6-Dinitro-4-methylchlorobenzene in methanol is allowed to react with ethoxyamine hydrochloride in the presence of triethylamine for a sufficient time to bring about substantially complete reaction. This reaction is initiated at room temperature and the progress of the reaction is followed by thin layer chromatography (TLC) or by nuclear magnetic resonance spectroscopy (NMR) at about 30 minute intervals after the start of the reaction. Reaction times vary, and apparently are influenced by the identity of the 4-substituent of the 2,6-dinitrobenzene compound used in the reaction, the 4-trifluoromethyl-2,6-dinitrohalobenzene compounds being very reactive. The reaction times therefore vary from about an hour or so at room temperature to as much as about 18 hours at reflux temperature in the case where the reactants are less reactive. When the reaction appears to be substantially completed, the reaction mixture is worked up to yield the desired product, which, in the instant example, is identified as 2,6-dinitro-N-ethoxy-p-toluidine, having a melting point of about 64°–66° C. The novel N-alkoxy compounds obtained by this process are useful as intermediates in the preparation of other novel compounds coming within the scope of generic formula (I), supra, which compounds possess herbicidal activity. Some of these novel intermediate compounds are also herbicidal in their activity.

When used as an intermediate, one of these compounds is allowed to react with a suitable alkylating agent in the presence of sodium hydride as the base, using dimethylformamide as the solvent of choice. Suitable alkylating agents include $C_1$–$C_3$ alkyl halides such as methyl iodide, methyl bromide, methyl chloride, ethyl iodide, ethyl bromide, ethyl chloride, n-propyl bromide, n-propyl chloride, n-propyl iodide, isopropyl bromide, isopropyl chloride, isopropyl iodide; $C_1$–$C_3$ alkyl sulfates such as methyl sulfate, ethyl sulfate, n-propyl sulfate, isopropyl sulfate; $C_3$–$C_4$ alkenyl halides such as allyl bromide, allyl chloride, crotyl chloride, crotyl bromide, methallyl chloride and methallyl bromide. This preparation is illustrated as follows. A mixture of 2,6-dinitro-N-ethoxy-p-toluidine and sodium hydride in dimethylformamide is allowed to stir at room temperature for a short period of time, suitably about 10 minutes. At the end of that time the alkylating agent, for example, allyl bromide, is added to the reaction mixture, and the mixture is stirred for such period of time as to bring about substantially complete reaction. The progress of the reaction is checked at about 30 minute intervals by thin-layer chromatography (TLC). A suitable period to allow for reaction is from about 0.5 to about 12 hours.

The reaction product mixture is worked up by adding water and dilute aqueous acid, suitably dilute aqueous hydrochloric acid. In some cases the product precipitates or crystallizes out of the acidified mixture, and is filtered off. In other cases, a water-immiscible solvent, such as ethyl acetate, ether, benzene or toluene, is added to extract the product from the aqueous acidified mixture. The organic solution is separated and dried over a suitable drying agent, for example anhydrous magnesium sulfate. The drying agent is then filtered off and the filtrate concentrated in vacuo to remove the solvent and leave a residue. This residue is then dissolved in a suitable solvent, for example toluene, and chromatographed over a Florisil column using toluene as the eluent. The eluate from the column is concentrated and the residue thus obtained is identified by NMR spectrum and elemental analyses, in the instant example, as N-allyl-2,6-dinitro-N-ethoxy-p-toluidine.

The syntheses of the compounds of generic formula I, supra, are described in the Examples which follow.

EXAMPLE 1

2,6-Dinitro-N-ethoxy-p-toluidine

A suspension of 10.0 g. (0.046 mole) of 2,6-dinitro-4-methylchlorobenzene in 100 ml. of methanol was prepared, and to the suspension there was added 7.6 g. (0.092 mole) of ethoxyamine hydrochloride, and 13.9 g. (0.138 mole) of triethylamine. The reaction mixture was stirred for about 30 minutes at room temperature and then heated and stirred for about 30 minutes at about 50° C., after which an additional 16.7 g. (0.20 mole) of ethoxyamine hydrochloride was added, and the reaction mixture was stirred and refluxed for about 24 hours. An NMR spectrum of the reaction mixture indicated the presence of the desired product in about 70 percent yield. The reaction product mixture was poured over a mixture of ice and water, and the aqueous mixture filtered. The solid obtained was recrystallized from petroleum ether (b.p. 60°–71° C.) to yield 5.5 g. of product having a melting point of about 64°–66° C. The product was identified by its NMR spectrum as 2,6-dinitro-N-ethoxy-p-toluidine.

EXAMPLE 2

2,6-Dinitro-4-ethyl-N-methoxyaniline

A suspension of 10.0 g. (0.043 mole) of 2,6-dinitro-4-ethylchlorobenzene in 100 ml. of methanol was prepared, and to the suspension there was added 14.7 g. (0.176 mole) of methoxyamine hydrochloride, and 22.2 g. (0.22 mole) of triethylamine, and the mixture was refluxed overnight. An additional 14.7 g. (0.176 mole) of methoxyamine hydrochloride was added to keep the solution orange in color. The reaction product mixture was poured over ice and the aqueous mixture filtered. The solid which was collected was allowed to dry. It was recrystallized from petroleum ether (b.p. 60°–71° C.) to yield material weighing 7.0 g. and having a melting point of about 90° C. The product was identified by NMR spectrum and elemental analyses as 2,6-dinitro-4-ethyl-N-methoxyaniline.

Analyses: Calcd. for $C_9H_{11}N_3O_5$:

| | Theoretical | Found |
|---|---|---|
| C | 44.80% | 45.11% |
| H | 4.60 | 4.53 |
| N | 17.42 | 17.34 |

Following the same general procedure of Example 2 and using 21.6 g. (0.1 mole) of 2,6-dinitro-4-methylchlorobenzene, 12.5 g. (0.15 mole) of methoxyamine hydrochloride, and 25.25 g. (0.25 mole) of triethylamine, the following additional compound was prepared:

EXAMPLE 3

2,6-Dinitro-N-methoxy-p-toluidine, having a melting point of about 141°–143° C., and identified by NMR spectrum and elemental analyses. Yield = 12.5 g.

Analyses: Calcd. for $C_8H_9N_3O_5$:

| | Theoretical | Found |
|---|---|---|
| C | 42.30% | 42.50% |
| H | 3.99 | 3.87 |
| N | 18.50 | 18.42 |

EXAMPLE 4

2,6-Dinitro-N-ethoxy-α,α,α-trifluoro-p-toluidine

A solution of 10.0 g. (0.037 mole) of 4-chloro-3,5-dinitrobenzotrifluoride in 100 ml. of ethanol was prepared, to which there was added 11.21 g. (0.111 mole) of triethylamine, followed, in about 30 seconds, by the addition of 4.46 g. (0.046 mole) of ethoxyamine hydrochloride. The reaction mixture was allowed to stir at ambient room temperature for about one and a quarter hours and additional ethoxyamine hydrochloride, 4.46 g. (0.046 mole), was added, bringing about a color change of the reaction mixture and the evolution of heat. The reaction product mixture was then worked up by diluting it with water, making the solution acidic with dilute aqueous hydrochloric acid and extracting the solution with several portions of ether. The combined ether extracts were washed several times with dilute aqueous hydrochloric acid and water, and dried over anhydrous magnesium sulfate. The drying agent was filtered off and the filtrate was concentrated in vacuo to leave a residue. The residue was recrystallized from petroleum ether (b.p. 60°–71° C.) to yield a product having a melting point of about 96°–98° C., and weighing 9.0 g. The product was identified by NMR spectrum and elemental analyses as 2,6-dinitro-N-ethoxy-α,α,α-trifluoro-p-toluidine.

Analyses: Calcd. for $C_9H_8F_3N_3O_5$:

| | Theoretical | Found |
|---|---|---|
| C | 36.62% | 36.66% |
| H | 2.73 | 2.47 |
| N | 14.24 | 14.09 |

EXAMPLE 5

2,6-Dinitro-N-methoxy-α,α,α-trifluoro-p-toluidine

To a solution prepared from 27.0 g. (0.1 mole) of 4-chloro-3,5-dinitrobenzotrifluoride in 200 ml. of ethanol there was added 25.25 g. (0.25 mole) of triethylamine, and 12.5 g. (0.15 mole) of methoxyamine hydrochloride. Upon the addition of the methoxyamine hydrochloride, the temperature of the reaction mixture rose to about 50° C. The reaction mixture was allowed to stir for about 1½ hours and the reaction product mixture was worked up by diluting with ethyl acetate, washing several times with dilute hydrochloric acid and water, and drying the organic layer over anhydrous magnesium sulfate. The drying agent was filtered off and the filtrate concentrated on the steam bath to leave a residue. The residue was allowed to chill over the weekend in the refrigerator and crystals separated. The crystalline product was filtered off. It had a melting point of about 135°–137° C., weighed 21.0 g., and was identified by NMR spectrum and elemental analyses as 2,6-dinitro-N-methoxy-α,α,α-trifluoro-p-toluidine.

| Analyses: Calcd. for $C_8H_6F_3N_3O_5$: | | |
|---|---|---|
| | Theoretical | Found |
| C | 34.18% | 34.17% |
| H | 2.15 | 2.12 |
| N | 14.95 | 14.82 |

EXAMPLE 6

N-Allyl-2,6-dinitro-N-ethoxy-p-toluidine

A mixture of 2.5 g. (0.01 mole) of 2,6-dinitro-N-ethoxy-p-toluidine (see Example 1) and 0.015 mole of sodium hydride (prepared from 0.72 g. of a 50% dispersion of sodium hydride in mineral oil by repeated washings with hexane) in 75 ml. of dimethylformamide was prepared and allowed to stir for about 10 minutes at room temperature. At the end of that time, 2.42 g. (0.02 mole) of allyl bromide was added to the reaction mixture. The mixture was stirred for about one hour at room temperature. The reaction product mixture was worked up by adding ether and washing with aqueous hydrochloric acid. The organic solution was dried over anhydrous magnesium sulfate, filtered, and the filtrate concentrated in vacuo to remove the solvent. The residue thus obtained was dissolved in toluene and chromatographed over a Florisil column, using toluene as the eluent. The solution collected from the column was concentrated and there was obtained 1.25 g. of an oil which was identified by its NMR spectrum and elemental analyses as N-allyl-2,6-dinitro-N-ethoxy-p-toluidine.

| Analyses: Calcd. for $C_{12}H_{15}N_3O_5$: | | |
|---|---|---|
| | Theoretical | Found |
| C | 51.24% | 51.37% |
| H | 5.38 | 5.10 |
| N | 14.94 | 14.70 |

Following the same general procedure of Example 6, and using appropriate starting materials, as indicated, the following additional compounds were prepared and identified by NMR spectra and elemental analyses:

EXAMPLE 7

2,6-Dinitro-N-ethoxy-N-propyl-p-toluidine, as an oil weighing 1.2 g., from 5.0 g. (0.021 mole) of 2,6-dinitro-N-ethoxy-p-toluidine (Example 1), 3.39 g. (0.0203 mole) of n-propyl iodide, and 0.012 mole of sodium hydride, prepared from 0.59 g. of a 50% dispersion of sodium hydride in mineral oil.

| Analyses: Calcd. for $C_{12}H_{17}N_3O_5$: | | |
|---|---|---|
| | Theoretical | Found |
| C | 50.88% | 50.60% |
| H | 6.05 | 5.80 |

| -continued | | |
|---|---|---|
| Analyses: Calcd. for $C_{12}H_{17}N_3O_5$: | | |
| | Theoretical | Found |
| N | 14.83 | 14.57 |

EXAMPLE 8

N,4-Diethyl-2,6-dinitro-N-methoxyaniline, weighing 1.0 g., and having a melting point of about 80°–82° C., from 5.0 g. (0.021 mole) of 2,6-dinitro-4-ethyl-N-methoxyaniline (Example 2), 0.02 mole of sodium hydride obtained from 0.96 g. of a 50% dispersion of sodium hydride in mineral oil, and 6.24 g. (0.04 mole) of ethyl iodide.

| Analyses: Calcd. for $C_{11}H_{15}N_3O_5$: | | |
|---|---|---|
| | Theoretical | Found |
| C | 49.07% | 49.19% |
| H | 5.62 | 5.37 |
| N | 15.61 | 15.42 |

EXAMPLE 9

2,6-Dinitro-4-ethyl-N-methoxy-N-propylaniline, having a melting point of about 72°–74° C., and weighing 1.5 g., from 3.0 g. (0.0124 mole) of 2,6-dinitro-4-ethyl-N-methoxyaniline (Example 2), 4.0 g. (0.024 mole) of n-propyl iodide, and 0.012 mole of sodium hydride obtained from 0.58 g. of a 50% dispersion of sodium hydride in mineral oil.

| Analyses: Calcd. for $C_{12}H_{17}N_3O_5$: | | |
|---|---|---|
| | Theoretical | Found |
| C | 50.88% | 51.01% |
| H | 6.05 | 5.80 |
| N | 14.83 | 14.82 |

EXAMPLE 10

2,6-Dinitro-N-ethyl-N-methoxy-α,α,α-trifluoro-p-toluidine

To 0.017 mole of sodium hydride, obtained from 0.82 g. of a 50% dispersion of sodium hydride in mineral oil, was added 50 ml. of dimethylformamide. To the mixture there was added 5.0 g. (0.018 mole) of 2,6-dinitro-N-methoxy-α,α,α-trifluoro-p-toluidine (Example 5), and the mixture was heated for about 45 minutes at temperatures up to about 65° C. The reaction mixture was then cooled to room temperature and there was added thereto, dropwise, 5.3 g. (0.034 mole) of ethyl iodide. The mixture was allowed to stir at room temperature for about 30 minutes and was then heated for about 1 hour at about 80° C., and was checked by TLC. No starting material appeared on the thin layer chromatogram. The reaction product mixture was cooled and allowed to stand overnight at ambient room temperature. The reaction product mixture was worked up by diluting it with ether and washing several times with dilute aqueous hydrochloric acid, once with water, and drying the organic phase over anhydrous magnesium sulfate. The drying agent was filtered off and the solvent removed in vacuo. The residue was chromatographed on a Florisil column using benzene both as solvent and as eluent. The first fractions collected appeared to contain the desired product. The fractions were combined, the solvent was removed in vacuo, and the residue thus obtained was recrystallized from petroleum ether (b.p. 60°–71° C.). The product had a melting point of about 95°–97° C., weighed 1.0 g., and was identified by NMR spectrum and elemental analyses as 2,6-dinitro-N-ethyl-N-methoxy-α,α,α-trifluoro-p-toluidine.

| Analyses: Calcd. for $C_{10}H_{10}F_3N_3O_5$: | | |
|---|---|---|
| | Theoretical | Found |
| C | 38.85% | 39.86% |
| H | 3.26 | 3.23 |
| N | 13.59 | 13.88 |

EXAMPLE 11

2,6-Dinitro-N-methoxy-N-propyl-α,α,α-trifluoro-p-toluidine

Petroleum ether (b.p. 60°–71° C.) was stirred with 0.82 g. of a 50% dispersion of sodium hydride in mineral oil, and the petroleum ether solution of the mineral oil was removed by decanting. The 0.017 mole of sodium hydride remaining was suspended in 75 ml. of dimethylformamide and 5.0 g. (0.018 mole) of 2,6-dinitro-N-methoxy-60 ,α,α-trifluoro-p-toluidine (Example 5) was added. The reaction mixture was heated for about 30 minutes to a temperature of about 65° C. The reaction mixture was then cooled to about room temperature and 5.78 g. (0.034 mole) of n-propyl iodide was added. The reaction mixture was heated to about 40° C. for a period of about 30 minutes, and the temperature was then gradually increased to about 100°–110° C. The heating time totaled about 2 hours. At the end of that time, the reaction product mixture was cooled and worked up by diluting it with ether and washing the mixture successively with dilute aqueous hydrochloric acid and water. The organic phase was dried over anhydrous magnesium sulfate. The drying agent was filtered off and the filtrate concentrated in vacuo to leave a residue. The residue was chromatographed on a Florisil column using benzene as solvent and eluent. The fractions from the column were concentrated to leave a residue and the residue was recrystallized from petroleum ether (b.p. 60°–71° C.) The product obtained weighed 1.9 g., and had a melting point of about 59°–60° C. The product was identified by NMR spectrum and elemental analyses as 2,6-dinitro-N-methoxy-N-propyl-α,α,α-trifluoro-p-toluidine.

| Analyses: Calcd. for $C_{11}H_{12}F_3N_3O_5$: | | |
|---|---|---|
| | Theoretical | Found |
| C | 40.88% | 40.68% |
| H | 3.74 | 3.84 |
| N | 13.00 | 13.20 |

EXAMPLE 12

2,6-Dinitro-N-methallyl-N-methoxy-α,α,α-trifluoro-p-toluidine

To 0.017 mole of sodium hydride, obtained from 0.82 g. of a 50% dispersion of sodium hydride in mineral oil (by the process described in Example 11, supra), was added 50 ml. of dimethylformamide. There was then added to the mixture of sodium hydride and dimethylformamide, 5.0 g. (0.018 mole) of 2,6-dinitro-N-methoxy-α,α,α-trifluoro-p-toluidine (Example 5), and the reaction mixture heated to about 60° C. for about 20 minutes. The reaction mixture was then cooled to approximately room temperature and there was added 6.14 g. (0.068 mole) of methallyl chloride. The reaction mixture was then heated to about 65° C. for about 30 minutes, following which the temperature of the reaction mixture was increased to about 90° C. and held there for about 2 hours, followed by heating for an additional 2 hours at about 110° C. The reaction product mixture was cooled, diluted with ether, and washed with dilute aqueous hydrochloric acid and water. The ether layer was dried over anhydrous magnesium sulfate. The drying agent was filtered off and the filtrate concentrated in vacuo to remove the solvent. The residue was dissolved in benzene and chromatographed on a Florisil column, using benzene as the eluant. The first portion off the column was concentrated in vacuo to leave a residue which was recrystallized from petroleum ether (b.p. 60°–71° C.). There was obtained material weighing 0.5 g. and having a melting point of about 55°–56° C. The material was identified by NMR spectrum and elemental analyses as 2,6-dinitro-N-methallyl-N-methoxy-α,α,α-trifluoro-p-toluidine.

| Analyses: Calcd. for $C_{12}H_{12}F_3N_3O_5$: | | |
|---|---|---|
| | Theoretical | Found |
| C | 42.99% | 42.75% |
| H | 3.61 | 3.39 |
| N | 12.53 | 12.31 |

Following the same general procedure of Example 12, and using appropriate starting materials, as indicated, the following additional compound was prepared and identified by NMR spectrum and elemental analyses:

EXAMPLE 13

N-Allyl-2,6-dinitro-N-methoxy-α,α,α-trifluoro-p-toluidine, weighing 2.4 g., and having a melting point of about 77°–79° C., from 5.0 g. (0.018 mole) of 2,6-dinitro-N-methoxy-α,α,α-trifluoro-p-toluidine (Example 5), 4.11 g. (0.034 mole) of allyl bromide, and 0.42 g. (0.017 mole) of sodium hydride, obtained from 0.82 g. of a 50% dispersion of sodium hydride in mineral oil.

| Analyses: Calcd. for $C_{11}H_{10}F_3N_3O_5$: | | |
|---|---|---|
| | Theoretical | Found |
| C | 41.13% | 41.15% |
| H | 3.14 | 3.09 |
| N | 13.08 | 12.83 |

EXAMPLE 14

2,6-Dinitro-N-ethoxy-N-ethyl-α,α,α-trifluoro-p-toluidine

To 0.017 mole of sodium hydride, obtained from 0.82 g. of a 50% dispersion of sodium hydride in mineral oil (by the process described in Example 11, supra), was added 50 ml. of dimethylformamide and 5.0 g. (0.017 mole) of 2,6-dinitro-N-ethoxy-α,α,α-trifluoro-p-toluidine (Example 4), and the mixture was stirred for about 20 minutes at room temperature. There was then added 5.3 g. (0.034 mole) of ethyl iodide and the reaction mixture was heated to about 85° C. for about 2.5 hours. The progress of the reaction was checked by NMR spectrum, which showed the presence of about 66 percent product and 33 percent starting material. Another 5.3 g. (0.034 mole) of ethyl iodide was added and the mixture was heated another one-half hour. The reaction product mixture was then allowed to cool and was diluted with ether. The ether mixture was washed several times with dilute aqueous hydrochloric acid, once with water, and dried over anhydrous magnesium sulfate. The drying agent was filtered off and the filtrate concentrated in vacuo to remove the solvent, leaving a residue. The residue was dissolved in benzene and chromatographed on a Florisil column using benzene as the eluant. The fractions which were collected were checked by NMR. The pure fractions were combined and the solvent evaporated to dryness. The product thus obtained weighed 0.65 g. and had a melting point of about 72°–75° C. The product was identified by NMR spectrum and elemental analyses as 2,6-dinitro-N-ethoxy-N-ethyl-α,α,α-trifluoro-p-toluidine.

| Analyses: Calcd. for $C_{11}H_{12}F_3N_3O_5$: | | |
|---|---|---|
| | Theoretical | Found |
| C | 40.88% | 41.09% |
| H | 3.74 | 3.44 |
| N | 13.00 | 12.88 |

Following the same general procedure of Example 14, and using appropriate starting materials, as indicated, the following additional compounds were prepared and identified by NMR spectrum and elemental analyses:

EXAMPLE 15

N-Allyl-2,6-dinitro-N-ethoxy-α,α,α-trifluoro-p-toluidine, weighing 1.15 g., and having a melting point of about 52°–54° C., from 5.0 g. (0.017 mole) of 2,6-dinitro-N-ethoxy-α,α,α-trifluoro-p-toluidine (Example 4), 4.11 g. (0.034 mole) of allyl bromide, and 0.017 mole of sodium hydride, obtained from 0.82 g. of a 50% dispersion of sodium hydride in mineral oil in the manner previously described.

| Analyses: Calcd. for $C_{12}H_{12}F_3N_3O_5$: | | |
|---|---|---|
| | Theoretical | Found |
| C | 42.99% | 42.77% |
| H | 3.61 | 3.72 |
| N | 12.53 | 12.80 |

EXAMPLE 16

2,6-Dinitro-N-ethoxy-N-propyl-α,α,α-trifluoro-N-p-toluidine, weighing 1.0 g., and having a melting point of about 34°–35° C., from 5.0 g. (0.017 mole) of 2,6-dinitro-N-ethoxy-α,α,α-trifluoro-p-toluidine (Example 4), 5.78 g. (0.034 mole) of n-propyl iodide, and 0.017 mole of sodium hydride, obtained in the usual manner from 0.82 g. of a 50% dispersion of sodium hydride in mineral oil.

| Analyses: Calcd. for $C_{12}H_{14}F_3N_3O_5$: | | |
|---|---|---|
| | Theoretical | Found |
| C | 42.74% | 42.99% |
| H | 4.18 | 4.36 |
| N | 12.46 | 12.59 |

EXAMPLE 17

2,6-Dinitro-N-ethyl-N-methoxy-p-toluidine

To 0.017 mole of sodium hydride, obtained from 0.82 g. of a 50% dispersion of sodium hydride in mineral oil (by the process described in Example 11, supra), was added 50 ml. of dimethylformamide to the sodium hydride, followed by 4.54 g. (0.02 mole) of 2,6-dinitro-N-methoxy-p-toluidine (Example 3), with continuous mechanical stirring. The temperature of the mixture rose to about 40° C. Stirring was continued for about 10 minutes, followed by addition of 12.48 g. (0.08 mole) of ethyl iodide. The temperature of the reaction mixture was increased to about 90° C., and stirring continued for about 30 minutes. The progress of the reaction was checked by running an NMR spectrum on a small sample of the reaction mixture, which NMR spectrum showed mostly product was present. The reaction product mixture was stirred and heated at about 90° C. for another 30 minutes. The reaction product mixture was allowed to cool and was diluted with ether. It was washed with dilute aqueous hydrochloric acid and then with water. The organic layer was dried over anhydrous magnesium sulfate, the drying agent filtered off, and the solvent removed in vacuo. The residue was recrystallized from a mixture of petroleum ether (b.p. 60°–71° C.)-ethyl acetate, to yield product having a melting point of about 47°–50° C., and weighing 1.7 g. The product was identified by NMR spectrum and elemental analyses as 2,6-dinitro-N-ethyl-N-methoxy-p-toluidine.

| Analyses: Calcd. for $C_{10}H_{13}N_3O_5$: | | |
|---|---|---|
| | Theoretical | Found |
| C | 47.06% | 47.06% |
| H | 5.13 | 5.02 |
| N | 16.46 | 16.46 |

Following the same general procedure of Example 17, and using appropriate starting materials, as indicated, the following additional compounds were prepared and identified by NMR spectra and elemental analyses:

EXAMPLE 18

2,6-Dinitro-N-methoxy-N-propyl-p-toluidine, as an oil, weighing 0.8 g., from 2.0 g. (0.009 mole) of 2,6-dinitro-N-methoxy-p-toluidine (Example 3), 3.4 g. (0.02 mole) of n-propyl iodide, and 0.5 g. (0.01 mole) of a 50% dispersion of sodium hydride in mineral oil.

| Analyses: Calcd. for $C_{11}H_{15}N_3O_5$: | | |
|---|---|---|
| | Theoretical | Found |
| C | 49.07% | 49.30% |
| H | 5.62 | 5.36 |
| N | 15.61 | 15.62 |

EXAMPLE 19

N-allyl-2,6-dinitro-N-methoxy-p-toluidine, having a melting point of about 80°–82° C., and weighing 0.67 g., from 4.5 g. (0.02 mole) of 2,6-dinitro-N-methoxy-p-toluidine (Example 3), 4.8 g. (0.04 mole) of allyl bromide, and 0.96 g. (0.02 mole) of a 50% dispersion of sodium hydride in mineral oil.

| Analyses: Calcd. for $C_{11}H_{13}N_3O_5$: | | |
|---|---|---|
| | Theoretical | Found |
| C | 49.44% | 49.29 |
| H | 4.90 | 4.78 |
| N | 15.72 | 15.59 |

EXAMPLE 20

N-Allyl-2,6-dinitro-4-ethyl-N-methoxyaniline

To 0.017 mole of sodium hydride, obtained from 0.82 g. of a 50% dispersion of sodium hydride in mineral oil (by the process described in Example 11, supra), was added 50 ml. of dimethylformamide. To the suspension was added 3.0 g. (0.012 mole) of 2,6-dinitro-4-ethyl-N-methoxyaniline (Example 2), and the mixture stirred for about 5–10 minutes. Allyl bromide, 2.9 g. (0.024 mole), was added and the reaction mixture stirred at room temperature for about 30 minutes. A sample of the reaction mixture checked by NMR showed the presence of about 70–80 percent of the desired product, together with about 20–30 percent of starting material. The reaction mixture was then heated at about 90° C., with stirring, for about an hour. A check by NMR indicated the reaction had gone to completion. The reaction product mixture was worked up by adding dilute aqueous hydrochloric acid and toluene. The organic layer was separated and dried over anhydrous magnesium sulfate. The drying agent was filtered off and the filtrate was chromatographed on a Florisil column. The fractions were examined by NMR spectrum, combined, and concentrated in vacuo to dryness. The residue was recrystallized from petroleum ether (b.p. 60°–71° C.) to give 1.7 g. of product having a melting point of about 83°–85° C. The product was identified by NMR spectrum and elemental analyses as N-allyl-2,6-dinitro-4-ethyl-N-methoxyaniline.

| Analyses: Calcd. for $C_{12}H_{15}N_3O_5$: | | |
|---|---|---|
| | Theoretical | Found |
| C | 51.24% | 51.46% |
| H | 5.38 | 5.32 |
| N | 14.94 | 14.69 |

EXAMPLE 21

2,6-Dinitro-4-ethyl-N-methoxy-N-methylaniline

A suspension of 5.8 g. of (0.024 mole) of 2,6-dinitro-4-ethyl-N-methoxyaniline (Example 2), and 1.15 g. (0.024 mole) of a 50% dispersion of sodium hydride in mineral oil was prepared in 50 ml. of dimethylformamide. The mixture was stirred for about 10 minutes at room temperature, during which time the reaction temperature rose to about 50° C. There was then added 6.76 g. (0.048 mole) of methyl iodide, with continued stirring for about 30 minutes, during which time the temperature of the reaction mixture rose to about 90° C., with no external heating. The reaction mixture was checked by TLC, which showed the absence of starting material. The reaction product mixture was allowed to cool. The mixture was diluted with dilute aqueous hydrochloric acid and toluene, the organic layer separated, and dried over anhydrous magnesium sulfate. The drying agent was filtered off and the filtrate was chromatographed on a Florisil column, using toluene as the eluant. Two products came off the column at the same time. The mixture of two compounds was dissolved in a 75 percent benzene:25 percent petroleum ether (b.p. 60°–71° C.) mixture, and again chromatographed on a Florisil column. Fractions were collected from the column and checked by their NMR spectra. The desired product was the second to come off the column. The fractions containing the desired product were combined, concentrated in vacuo, and the residue thus obtained was recrystallized from petroleum ether (b.p. 60°–71° C.) to yield product weighing 0.7 g., and having a melting point of about 85°–87° C. The product was identified by NMR spectrum and elemental analyses as 2,6-dinitro-4-ethyl-N-methoxy-N-methylaniline.

| Analyses: Calcd. for $C_{10}H_{13}N_3O_5$: | | |
|---|---|---|
| | Theoretical | Found |
| C | 47.06% | 47.05% |
| H | 5.13 | 4.98 |
| N | 16.46 | 16.70 |

The novel compounds of this invention are used as herbicides in accordance with procedures well known in the agricultural art. For such use the compounds are formulated into compositions desirably containing, in addition to the substituted 2,6-dinitroaniline, one or more of a plurality of additaments including water, polyhydroxy compounds, petroleum distillates, and other dispersion media, surface-active dispersing agents, emulsifiers, and finely-divided inert solids. The concentration of the substituted 2,6-dinitroanilines in these compositions may vary depending on whether the composition is intended as an emulsifiable concentrate or a wettable powder designed to be subsequently diluted with additional inert carrier, such as water, to produce the ultimate treating composition, or is intended for direct application as a dust to plants.

Thus, treating compositions are most conveniently formulated by preparing liquid or solid concentrates, which are subsequently diluted to the desired level for use. Emulsifiable liquid concentrates can be prepared by incorporating from about 1 to about 30 percent by weight of the active ingredient, and an emulsifying agent, in a suitable water-immiscible organic liquid. Such concentrates may be further diluted with water to form spray mixtures in the form of oil-in-water emulsions. Such spray compositions then comprise active herbicide, water-immiscible solvent, emulsifying agent, and water. Suitable emulsifying agents can be of the nonionic or ionic types, or blends thereof, and include condensation products of alkylene oxides with phenols and organic acids, polyoxyethylene derivatives of sorbitan esters, such as polyoxyethylene sorbitan mono-oleate and polyoxyethylene sorbitan mono-laurate; complex ether alcohols, such as polyglycol ether sulfonate; ionics of the aralkyl sulfonate type, such as alkylamine dodecylbenzene sulfonate, and the like. Suitable water-immiscible organic liquids to be employed include aromatic hydrocarbons, aliphatic hydrocarbons, cycloaliphatic hydrocarbons and mixtures thereof, such as petroleum distillates.

Solid concentrate mixtures can be prepared by incorporating from about 1 to about 90% by weight of the substituted 2,6-dinitroaniline in a finely-divided inert solid carrier such as bentonite, fuller's earth, diatomaceous earth, silica, expanded mica, talc, chalk, and the like. Dispersing and/or wetting agents can be incorporated along with the substituted 2,6-dinitroaniline in the solid carrier to form wettable powder concentrates ranging from about 1 to about 75% by weight concentration, which subsequently can be dispersed in water or other hydroxylated carrier to form spray compositions. Suitable surfactants include condensed arylsulfonic acids and sodium salts thereof, sodium lignosulfate, sulfonate oxide condensate blends, alkylaryl polyether alcohols, sulfonated nonionic blends, anionic wetting agents, and the like.

Spreadable granules can be prepared using calcined attapulgite clay as the solid diluent. Dry dispersions can be prepared on herbicidally inert carriers, such as vermiculite, peat moss and the like.

The novel compounds of this invention can be used for treating a soil area or locus infested with seeds with a dust, granular formulation, or spray containing one or more of the novel compounds as the herbicidally-active ingredient. Typical of soil areas which can be treated are crop growing areas in which tolerant crops are being grown; and in miscellaneous places, such as gravel driveways, clay tennis courts, walks, road shoulders, and the like, where the elimination of weeds is desired. As is well understood in the art, the application rates required when the compounds are to be used in the field are greater than those mentioned above as being required in the greenhouse. In the use of the invention on a practical basis, compositions containing the herbicidally-active compound can be sprayed, dusted, or spread by methods well known to the art onto the particular area at the rate of from about 1.12 kg./ha. to about 36 kg./ha., or somewhat more if necessary, for example, about 56 kg. of active ingredient per hectare.

The herbicidal activity of the novel compounds of this invention has been established by tests which have been carried out as described hereinafter.

Test 1

A soil was prepared consisting of one part masonry sand and one part shredded top soil blended together. Plantings were made in galvanized metal flats which measured 31.5 cm. long, 21.5 cm. wide, and 8 cm. deep, with holes and grooves in the bottom for drainage. Each flat was filled two-thirds full with soil and the soil was leveled and tamped. All the seeds were planted in rows perpendicular to the long axis of the flat, one species per row. The large seeds of morningglory and corn were planted in rows about 1 cm. deep made by a hand-held press. The remainder of the seeds, that is, the small seeds, were planted by sprinkling the seeds in rows on the surface of the prepared soil in the trays, and then all of the seeds were covered with from 0.5 cm. to 1.0 cm. of sifted soil. The species planted (identified by letter) and the approximate number of seeds planted per species are as follows:

A - Corn (*Zea mays*) 4
B - Large crabgrass (*Digitaria sanguinalis*) 350
C - Pigweed (*Amarantus retroflexus*) 350
D - Foxtail millet (*Setaria italica*) 200
E - Velvetleaf (*Abutilon theophrasti*) 100
F - Morningglory (*Ipomoea purpurea*) 25
G - Zinnia (*Zinnia elegans*) 20

Two and one-half g. of soluble fertilizer was applied to each flat during the first watering after planting. The postemergence flats were planted 10-13 days prior to treatment and were then placed in a growth chamber until the day of treatment. The flats were given 12-18 hours of light each day, depending on light intensity, and subjected to a temperature of 74°-80° F. The preemergence flats were planted the same day the treatments were applied. After treatment, all the flats were moved into a greenhouse.

The compounds studied in this test were applied at the rate of 8.96 kg./ha. The formulation for an application rate of 8.96 kg./ha. was accomplished by dissolving 120 mg. of the test compound in about 2.5 ml. of a solvent containing acetone and ethyl alcohol in a 1:1 ratio together with a small amount of Toximul R and S. The solution was then diluted with deionized water to a volume of about 25 ml. Toximul R and Toximul S are sulfonate/nonionic blends which are products of Stepan Chemical Company, Northfield, Illinois.

The herbicidal compositions were applied to each flat with a modified DeVilbiss atomizer hooked to an air source. In the preemergent test, the herbicidal compositions were sprayed on the surface of the soil in the flat after the seeds were planted. In the postemergent test, the herbicidal compositions were sprayed on the foliage of the plants 10-13 days after planting the seeds from which the plants grew. Twelve and one-half ml. of the composition under test was applied to each flat. This is equal to an 8.96 kg./ha. application rate.

After treatment, all the flats were transferred to the greenhouse for 12-13 days. Herbicidal effects were then rated on each plant species. The ratings were based on a 1 to 5 scale:
1 = no injury
2 = slight injury
3 = moderate injury
4 = severe injury
5 = death Table 1, which follows, sets forth the results of the testing of the compounds. In the table, column 1 identifies the compound by its operating example number or preparation number in the specification; column 2, the rate in terms of kg./ha. at which the compound was applied to the test flat; columns 3 to 9, the injury rating for particular plant seedlings. The test plants are identified by letters of the alphabet, as set forth hereinabove.

TABLE 1

| Comp. | Appln. Rate kg./ha. | Plant Injury Ratings |||||||||||||
|---|---|---|---|---|---|---|---|---|---|---|---|---|---|---|
| | | Preemergence |||||||Postemergence||||||
| | | A | B | C | D | E | F | G | A | B | C | D | E | F | G |
| 2 | 8.96 | 1 | 4 | 4 | 4 | 1 | 1 | 1 | 2 | 5 | 5 | 5 | 4 | 3 | 3 |
| 3 | 8.96 | 1 | 5 | 5 | 4 | 1 | 1 | 1 | 2 | 5 | 4 | 5 | 3 | 3 | — |
| 5 | 8.96 | 1 | 2 | 2 | 3 | 1 | 1 | 1 | 1 | 3 | 2 | 2 | 2 | 2 | 2 |
| 6 | 8.96 | 1 | 4 | 4 | 3 | 3 | 2 | 1 | 3 | 4 | 4 | 4 | 3 | 3 | 3 |
| 7 | 8.96 | 4 | 4 | 3 | 4 | 3 | 3 | 2 | 3 | 4 | 4 | 3 | 4 | 3 | 3 |
| 8 | 8.96 | 4 | 5 | 4 | 5 | 3 | 3 | 2 | 2 | 4 | 4 | 4 | 3 | 3 | 2 |
| 10 | 8.96 | 1 | 2 | 2 | 2 | 1 | 1 | 1 | 1 | 2 | 2 | 1 | 2 | 1 | 1 |
| 11 | 8.96 | 2 | 3 | 2 | 3 | 2 | 1 | 1 | 1 | 1 | 1 | 1 | 1 | 1 | 1 |
| 13 | 8.96 | 1 | 2 | 3 | 3 | 1 | 1 | — | 1 | 3 | 2 | 2 | 1 | 2 | 1 |
| 14 | 8.96 | 1 | 2 | 1 | 2 | 1 | 1 | 1 | 2 | 2 | 1 | 1 | 1 | 1 | 1 |
| 15 | 8.96 | 1 | 2 | 2 | 2 | 1 | 1 | 1 | 2 | 3 | 2 | 1 | 1 | 2 | — |
| 16 | 8.96 | 3 | 3 |   | 4 | 2 | 2 | — | 2 | 3 | 2 | 2 | 2 | 2 | 2 |
| 17 | 8.96 | 2 | 4 | 3 | 3 | 3 | 1 | 1 | 3 | 5 | 4 | 5 | 3 | 3 | — |
| 18 | 8.96 | 1 | 4 | 3 | 3 | 3 | 2 | 1 | 3 | 5 | 4 | 4 | 4 | 4 | 3 |
| 19 | 8.96 | 1 | 4 | 2 | 3 | 3 | 1 | 1 | 2 | 5 | 5 | 5 | 3 | 2 | 3 |
| 21 | 8.96 | 1 | 4 | 3 | 4 | 2 | 1 | 1 | 2 | 4 | 5 | 3 | 3 | 3 | 2 |

Test 2

Further testing of certain of the compounds falling within the scope of the above generic formula as preemergent herbicides was carried out against a broader spectrum of plants. The plant species used in this experiment were planted in galvanized pans exactly like those used in Test 1, using the same type of soil. Each flat was filled two-thirds with the prepared soil and the soil leveled and tamped. In these preemergence tests, two flats containing ten indicator species each were used for each application rate of each chemical. The seeds of the species of plants were planted in rows parallel to the long axis of the flat, one species per half row, in the same manner as in Test 1. The approximate numbers of seeds planted are as follows:

A — Corn (*Zea mays*) 4
B — Cotton (*Gossypium hirsutum*) 6
C — Soybean (*Glycine max*) 6
D — Wheat (*Triticum aesitivum*) 40
E — Alfalfa (*Medicago sativa*) 100
F — Sugarbeet (*Beta vulgaris*) 25
G — Rice (*Oryza sativa*) 46
H — Cucumber (*Cucumis sativus*) 8
J — Tomato (*Lycopersicon esculentum*) 30
K — Barnyardgrass (*Echinochloa crusgalli*) 50
L — Lambsquarter (*Chenopodium album*) 100
M — Large crabgrass (*Digitaria sanguinalis*) 100
N — Mustard (*Brassica juncea*) 50
O — Pigweed (*Amaranthus retroflexus*) 150
P — Foxtail millet (*Setaria italica*) 100
Q — Wild oat (*Avena fatua*) 25
R — Velvetleaf (*Abutilon theophrasti*) 25
S — Jimsonweed (*Datura stramonium*)
T — Morningglory (*Ipomoea purpurea*) 15
U — Zinnia (*Zinnia elegans*) 20

For this preemergence testing, the flats were planted the same day as the treatments were applied, and the seeds were covered with 0.5 to 1.0 cm. of soil. The chemicals were formulated the same way as described in Test 1 and then serially diluted to provide the desired concentrations of test solutions for applications at the desired rate. Chemicals were applied to the surface of the flats using a modified DeVilbiss atomizer connected to an air source. Each flat received 12.5 ml. of spray solution. The flats were maintained in the greenhouse after the treatment.

The herbicidal effects of the chemicals were evaluated about 18–21 days after preemergence applications. The degree of plant injury is based on a 1 to 5 scale, the same as used in Test 1 hereinbefore.

Table 2, which follows, sets forth the results of the preemergent testing of the compounds against crops, grasses, and broadleaf weeds. In the table, column 1 identifies the compound; column 2, the rate in terms of kg./ha. at which the compound was applied to the test flat; and the remainder of the columns, the injury rating for the particular plant seedlings.

TABLE 2

| Compound | Appln. Rate kg./ha. | A | B | C | D | E | F | G | H | J | K | L | M | N | O | P | Q | R | S | T | U |
|---|---|---|---|---|---|---|---|---|---|---|---|---|---|---|---|---|---|---|---|---|---|
| 2 | 2.24 | 1 | 1 | 1 | 1 | 1 | 1 | 1 | 1 | 1 | .1 | 2 | 3 | 1 | 2 | 2 | 1 | 1 | 1 | 1 | 1 |
|  | 4.48 | 1 | 1 | 1 | 1 | 1 | 1 | 1 | 1 | 1 | 4 | 3 | 4 | 2 | 4 | 3 | 1 | 1 | 1 | 1 | 1 |
| 3 | 2.24 | 1 | 1 | 1 | 1 | 1 | 1 | 1 | 1 | 1 | 3 | 2 | 3 | 1 | 3 | 2 | 1 | 2 | 1 | 1 | 1 |
|  | 4.48 | 1 | 1 | 1 | 1 | 1 | 1 | 1 | 2 | 2 | 4 | 3 | 4 | 1 | 4 | 2 | 1 | 2 | 2 | 1 | 1 |
| 6 | 1.12 | 1 | 1 | 1 | 1 | 1 | 1 | 1 | 1 | 1 | 4 | 1 | 2 | 1 | 2 | 2 | 1 | 1 | 1 | 1 | 1 |
|  | 2.24 | 1 | 1 | 1 | 1 | 1 | 1 | 1 | 1 | 1 | 4 | 2 | 4 | 1 | 3 | 3 | 1 | 1 | 1 | 1 | 1 |
|  | 4.48 | 1 | 2 | 1 | 1 | 1 | 2 | 1 | 1 | 3 | 4 | 3 | 5 | 2 | 4 | 4 | 1 |  | 1 | 1 | 1 |
| 7 | 1.12 | 1 | 1 | 1 | 1 | 1 | 1 | 1 | 1 | 1 | 3 | 3 | 4 | 1 | 3 | 3 | 1 | 1 | 1 | 1 | 1 |
|  | 2.24 | 1 | 1 | 1 | 1 | 1 | 1 | 2 | 1 | 2 | 4 | 4 | 5 | 1 | 3 | 3 | 3 | 2 | 1 | 1 | 1 |
|  | 4.48 | 1 | 1 | 1 | 2 | 2 | 3 | 2 | 2 | 3 | 4 | 4 | 5 | 2 | 4 | 4 | 4 | 2 | 2 | 2 | 2 |
| 8 | 1.12 | 1 | 1 | 1 | 1 | 1 | 1 | 1 | 1 | 1 | 2 | 3 | 4 | 1 | 1 | 2 | 2 | 1 | 1 | 1 | 1 |
|  | 2.24 | 1 | 1 | 1 | 1 | 1 | 1 | 1 | 1 | 1 | 4 | 4 | 5 | 1 | 2 | 3 | 3 | 2 | 1 | 1 | 1 |
|  | 4.48 | 2 | 1 | 1 | 2 | 1 | 3 | 1 | 2 | 2 | 5 | 5 | 5 | 2 | 4 | 4 | 4 | 3 | 2 | 1 | 1 |
| 21 | 2.24 | 1 | 1 | 1 | 1 | 1 | 1 | 1 | 1 | 1 | 1 | 2 | 2 | 1 | 2 | 2 | 2 | 1 | 1 | 1 | 1 |
|  | 4.48 | 1 | 1 | 1 | 1 | 2 | 2 | 1 | 1 | 1 | 4 | 2 | 4 | 1 | 3 | 3 | 2 | 2 | 1 | 1 | 1 |

Test 3

The same compounds as were tested in Test 2, as well as some additional, were also tested as postemergent herbicides against the seven indicator species plants used in Test 1, following the same postemergence test procedure already described in Test 1.

The herbicidal effects of the chemicals were evaluated about 12 to 14 days after postemergence applications. The degree of plant injury is based on a 1 to 5 scale as set forth in the previous tests.

Table 3, which follows, sets forth the results of the postemergent testing of the compounds against the indicator species named above.

TABLE 3

Plant Injury Ratings
Postemergence

| Comp. | Appln. Rate kg./ha. | A | B | C | D | E | F | G |
|---|---|---|---|---|---|---|---|---|
| 2 | 1.12 | 2 | 3 | 3 | 3 | 1 | 2 | 2 |
|  | 2.24 | 2 | 4 | 4 | 3 | 2 | 3 | 2 |
|  | 4.48 | 2 | 4 | 4 | 3 | 2 | 3 | 3 |
| 3 | 1.12 | 1 | 3 | 2 | 4 | 2 | 2 | 2 |
|  | 2.24 | 2 | 3 | 3 | 3 | 1 | 1 | 2 |
|  | 4.48 | 1 | 4 | 4 | 4 | 2 | 2 | 2 |
| 6 | 1.12 | 1 | 2 | 1 | 1 | 1 | 1 | 1 |
|  | 2.24 | 1 | 2 | 2 | 2 | 1 | 1 | 1 |
|  | 4.48 | 2 | 2 | 3 | 3 | 2 | 2 | 2 |
| 7 | 1.12 | 1 | 2 | 1 | 1 | 1 | 1 | 1 |
|  | 2.24 | 1 | 2 | 1 | 2 | 1 | 1 | 1 |
|  | 4.48 | 2 | 3 | 2 | 2 | 3 | 2 | 2 |
| 8 | 1.12 | 1 | 2 | 1 | 1 | 1 | 1 | 1 |
|  | 2.24 | 2 | 2 | 1 | 2 | 1 | 1 | 1 |
|  | 4.48 | 1 | 3 | 3 | 2 | 1 | 2 | 1 |
| 17 | 1.12 | 1 | 2 | 1 | 1 | 1 | 1 | 2 |
|  | 2.24 | 2 | 2 | 2 | 3 | 2 | 2 | 2 |
|  | 4.48 | 2 | 2 | 3 | 3 | 3 | 2 | 2 |
| 18 | 1.12 | 2 | 2 | 2 | 2 | 2 | 1 | 1 |
|  | 2.24 | 2 | 3 | 3 | 3 | 3 | 2 | 2 |
|  | 4.48 | 2 | 4 | 3 | 4 | 4 | 3 | 3 |
| 19 | 1.12 | 1 | 2 | 2 | 2 | 2 | 1 | 2 |
|  | 2.24 | 2 | 3 | 2 | 3 | 3 | 2 | 2 |
|  | 4.48 | 2 | 3 | 3 | 3 | 3 | 2 | 2 |
| 21 | 2.24 | 1 | 2 | 2 | 1 | 1 | 1 | 1 |
|  | 4.48 | 2 | 3 | 4 | 3 | 2 | 2 | 2 |

The test results set forth in the Tables show that the novel compounds of this invention possess herbicidal activity.

We claim:

1. A compound of the formula

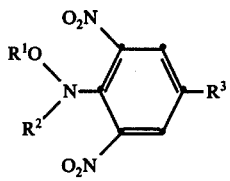

wherein
R¹ is methyl or ethyl;
R² is hydrogen, $C_1$–$C_3$ alkyl or $C_3$–$C_4$ alkenyl; and
R³ is methyl, ethyl, or trifluoromethyl.

2. A compound as in claim 1, said compound being 2,6-dinitro-N-ethoxy-N-propyl-p-toluidine.

3. A compound as in claim 1, said compound being 2,6-dinitro-4-ethyl-N-methoxy-N-methylaniline.

4. A compound as in claim 1, said compound being N-allyl-2,6-dinitro-N-ethoxy-p-toluidine.

5. A compound as in claim 1, said compound being 2,6-dinitro-N-ethoxy-N-propyl-α,α,α-trifluoro-p-toluidine.

6. A compound as in claim 1, said compound being N,4-diethyl-2,6-dinitro-N-methoxyaniline.

7. A compound as in claim 1, said compound being 2,6-dinitro-N-methoxy-N-propyl-p-toluidine.

8. A compound as in claim 1, said compound being 2,6-dinitro-N-ethoxy-α,α,α-trifluoro-p-toluidine.

9. A compound as in claim 1, said compound being 2,6-dinitro-N-methoxy-α,α,α-trifluoro-p-toluidine.

10. A compound as in claim 1, said compound being 2,6-dinitro-N-methoxy-p-toluidine.

11. A compound as in claim 1, said compound being 2,6-dinitro-4-ethyl-N-methoxyaniline.

12. A compound as in claim 1, said compound being 2,6-dinitro-N-ethoxy-p-toluidine.

UNITED STATES PATENT OFFICE
CERTIFICATE OF CORRECTION

Patent No. 4,087,460           Dated May 2, 1978

Inventor(s) Herschel D. Porter and James C. Williams

It is certified that error appears in the above-identified patent and that said Letters Patent are hereby corrected as shown below:

Column 14, Compound 16, Table 1, Preemergence, Column C: Insert the number --2--.

Column 16, Compound 3, Appln Rate 4.48, Table 2, Column P: Change the number "2" to number --3--.

Column 16, Compound 6, Appln Rate 4.48, Table 2, Column R: Insert the number --2--.

Column 7, line 24: "60,$\alpha$,$\alpha$" should read --$\alpha$,$\alpha$,$\alpha$--.

Column 13, line 49: "(Amarantus" should read --Amaranthus--.

Signed and Sealed this

Twenty-fourth Day of April 1979

[SEAL]

Attest:

RUTH C. MASON
Attesting Officer

DONALD W. BANNER
Commissioner of Patents and Trademarks